United States Patent [19]
Cohen

[11] Patent Number: 5,814,570
[45] Date of Patent: Sep. 29, 1998

[54] NONWOVEN BARRIER AND METHOD OF MAKING THE SAME

[75] Inventor: Bernard Cohen, Berkeley Lake, Ga.

[73] Assignee: Kimberly-Clark Worldwide, Inc., Neenah, Wis.

[21] Appl. No.: 648,451

[22] Filed: May 15, 1996

Related U.S. Application Data

[63] Continuation of Ser. No. 266,293, Jun. 27, 1994, abandoned.

[51] Int. Cl.$^6$ ...................................................... B32B 5/06
[52] U.S. Cl. .......................... 442/346; 204/164; 442/340; 442/351; 442/382; 428/903
[58] Field of Search .................................... 442/340, 346, 442/351, 382; 428/903; 204/164

[56] References Cited

U.S. PATENT DOCUMENTS

| | | | |
|---|---|---|---|
| Re. 30,782 | 10/1981 | van Turnhout | 264/22 |
| Re. 31,285 | 6/1983 | van Turnhout et al. | 55/155 |
| Re. 32,171 | 6/1986 | van Turnhout | 55/155 |

(List continued on next page.)

FOREIGN PATENT DOCUMENTS

| | | | |
|---|---|---|---|
| 1188452 | 6/1985 | Canada | A41D 13/00 |
| 0 125 851 | 11/1984 | European Pat. Off. | D21C 9/00 |
| 0 156 160 | 10/1985 | European Pat. Off. | A61L 15/00 |
| 0 391 725 | 4/1989 | European Pat. Off. . | |
| 0 334 829 | 9/1989 | European Pat. Off. . | |
| 0 337 662 | 10/1989 | European Pat. Off. . | |
| 0 375 234 | 6/1990 | European Pat. Off. . | |
| 0391725 | 10/1990 | European Pat. Off. . | |
| 0 444 671 | 9/1991 | European Pat. Off. . | |
| 0 462 574 | 12/1991 | European Pat. Off. . | |
| 0 550 029 | 12/1991 | European Pat. Off. . | |
| 0 478 011 | 4/1992 | European Pat. Off. | A61F 13/15 |
| 0 497 072 | 8/1992 | European Pat. Off. | A61F 13/15 |
| 0 520 798 | 12/1992 | European Pat. Off. | D04H 1/42 |
| 0550029 | 7/1993 | European Pat. Off. . | |
| 0 575 629 | 12/1993 | European Pat. Off. . | |
| 0 576 738 | 1/1994 | European Pat. Off. | A61F 13/15 |
| 0 594 123 | 4/1994 | European Pat. Off. . | |
| 1 084 015 | 9/1957 | Germany | 156/276 |
| 44 47 152 | 7/1995 | Germany | A61L 15/60 |
| 58-076118 | 7/1958 | Japan . | |
| 62-053719 | 8/1987 | Japan . | |
| 62-074423 | 9/1987 | Japan . | |
| 1-246413 | 10/1989 | Japan . | |
| 5-064713 | 3/1993 | Japan . | |
| 2 026 379 | 2/1980 | United Kingdom | D06M 9/00 |
| 2 242 142 | 9/1991 | United Kingdom | B03C 3/28 |
| WO8103265 | 11/1981 | WIPO . | |
| 90/11784 | 10/1990 | WIPO . | |
| 91/08254 | 6/1991 | WIPO . | |
| 92/16681 | 10/1992 | WIPO | D04H 1/42 |
| 93/06168 | 4/1993 | WIPO . | |
| 93/09156 | 5/1993 | WIPO | C08G 8/18 |
| 94/00166 | 1/1994 | WIPO . | |
| 94/01068 | 1/1994 | WIPO . | |
| 95/05232 | 2/1995 | WIPO . | |
| 95/05501 | 2/1995 | WIPO . | |
| 95/22646 | 8/1995 | WIPO . | |
| 96/00093 | 1/1996 | WIPO . | |

OTHER PUBLICATIONS

J. van Turnhout: Topics in Applied Physics, vol. 33, Chapter 3 "Thermally Stimulated Discharge of Electrets", pp. 81–215 (1980).

J. van Turnhout: Thermally Stimulated Discharge of Polymer Electrets, Chapter 1, pp. 1–24 (1975).

G.M. Sessler: Electronic Properties of Polymers, Chapter 3 "Charge Storage", pp. 59–107.

Database WPI, Week 8324, Derwent Publications Ltd., London, GB; AN 83–57499K & JP,A, 58 076 118 (Koken KK), 9 May 1983, See Abstract.

Database WPI, Section Ch, Week 8428, Derwent Publications Ltd., London, GB; Class A87, AN 84–173431, XP002008760, & JP,A,59 094 621 (Unitika KK), 31 May 1984, see abstract.

Patent Abstracts of Japan, vol. 10, No. 71 (C–334), 20 March 1986 & JP,A,60 209220 (Kouken K.K.), 21 Oct. 1985, see abstract.

Patent Abstracts of Japan, vol. 6, No. 191 (C–127), 30 Sep. 1982 & JP,A,57 105217 (Nitta K.K.), 30 Jun. 1982, see abstract & Chemical Abstracts, vol. 97, No. 26, 27 Dec. 1982, Columbus, Ohio, US; abstract No. 218901, "Fibrous Filtering Material", see abstract.

Patent Abstracts of Japan, vol. 11, No. 315 (C–451), 14 Oct. 1987 & JP,A,62 102809 (Mitsui Petrochem. Ind. Ltd.), 13 May 1987, see abstract & Database WPI, Section Ch, Week 8725, Derwent Publications Ltd., London, GB; Class A12, AN 87–172842 & JP,A,62 102 809 (Mitsui Petrochem. Ind. Co. Ltd.), 13 May 1987, see abstract.

Journal of Electrostatics, vol. 21, 1988, Amsterdam NL, pp. 81–98, XP002012022, P. A. Smith & G. C. East: "Generation of Triboelectric Charge in Textile Fibre Mistures, and their use as Air Filters", see document.

Database WPI, Section Ch, Week 8930, Derwent Publications, Ltd., London, GB; Class A94, AN 89–217687 XP002005648 & JP,A,01 156 578 (Showa Denko), 20 Jun. 1989, See Abstract.

An Introduction to Electrostatic Separation, Technical Bulletin, Bulletin 8570, Carpco, Inc.

Electrostatic Separation of Mixed Granular Solids by Oliver C. Ralston, Elsevier Publishing Company, 1961, Chapter IV, "Applications of Electrostatic Separation", pp. 134–234.

"Bonding Process", IBM Technical Disclosure Bulletin, vol. 14, No. 12, May 1972.

USSN 08/242,948 filed May 16, 1994 entitled "Nonwoven Absorbent Polymeric Fabric Exhibiting Improved Fluid Management And Methods For Making The Same".

*Primary Examiner*—James J. Bell
*Attorney, Agent, or Firm*—David J. Alexander; Jones & Askew, LLP

[57] ABSTRACT

A ethylene oxide sterilizable nonwoven material which is subjected to charging, and more particularly electrostatic charging is provided. The nonwoven materials may include laminate nonwovens wherein one or more layers are subjected to charging. The nonwoven material(s) may also be treated with an antistatic material before or after subjecting the same to charging.

19 Claims, No Drawings

U.S. PATENT DOCUMENTS

| | | | |
|---|---|---|---|
| 668,791 | 2/1901 | Blake et al. . | |
| 813,063 | 2/1906 | Sutton et al. . | |
| 859,998 | 7/1907 | Wentworth . | |
| 924,032 | 6/1909 | Blake et al. . | |
| 1,222,305 | 4/1917 | Kraus . | |
| 1,297,159 | 6/1919 | Hedberg . | |
| 1,355,477 | 10/1920 | Howell . | |
| 2,106,865 | 2/1938 | Bantz et al. | 209/127 |
| 2,217,444 | 10/1940 | Hill | 91/18 |
| 2,328,577 | 9/1943 | Oglesby | 117/17 |
| 2,378,067 | 3/1945 | Cook, Jr. | 209/127 |
| 2,398,792 | 4/1946 | Johnson | 209/127 |
| 2,748,018 | 5/1956 | Miller | 117/17 |
| 2,998,051 | 8/1961 | Sittel | 154/1.7 |
| 3,012,668 | 12/1961 | Fraas | 209/127 |
| 3,059,772 | 10/1962 | Baron | 209/127 |
| 3,125,547 | 3/1964 | Blatz | 260/45.5 |
| 3,281,347 | 10/1966 | Winder | 204/168 |
| 3,323,933 | 6/1967 | Barford et al. | 117/17 |
| 3,338,992 | 8/1967 | Kinney | 264/24 |
| 3,341,007 | 9/1967 | Mayer et al. | 209/2 |
| 3,341,394 | 9/1967 | Kinney | 161/72 |
| 3,380,584 | 4/1968 | Fulwyler | 209/3 |
| 3,402,814 | 9/1968 | Morel et al. | 209/127 |
| 3,436,797 | 4/1969 | Graf et al. | 156/272.6 |
| 3,502,763 | 3/1970 | Hartmann | 264/210 |
| 3,542,615 | 11/1970 | Dobo et al. | 156/181 |
| 3,581,886 | 6/1971 | Singewald et al. | 209/9 |
| 3,692,606 | 9/1972 | Miller et al. | 156/273.1 |
| 3,692,618 | 9/1972 | Dorschner et al. | 161/72 |
| 3,802,817 | 4/1974 | Matsuki et al. | 425/66 |
| 3,821,021 | 6/1974 | McMillan | 117/135.5 |
| 3,849,241 | 11/1974 | Butin et al. | 161/169 |
| 3,855,046 | 12/1974 | Hansen et al. | 161/150 |
| 3,859,330 | 1/1975 | Proskow | 260/47 UA |
| 3,896,802 | 7/1975 | Williams | 128/149 |
| 3,907,604 | 9/1975 | Prentice | 136/146 |
| 3,909,009 | 9/1975 | Cvetko et al. | 274/37 |
| 3,962,386 | 6/1976 | Driscoll | 264/22 |
| 3,979,529 | 9/1976 | Rebentisch et al. | 427/25 |
| 3,998,916 | 12/1976 | van Turnhout | 264/22 |
| 4,011,067 | 3/1977 | Carey, Jr. | 55/354 |
| 4,013,816 | 3/1977 | Sabee et al. | 428/288 |
| 4,035,164 | 7/1977 | Taylor . | |
| 4,041,203 | 8/1977 | Brock et al. | 428/157 |
| 4,058,724 | 11/1977 | McKinney et al. . | |
| 4,070,218 | 1/1978 | Weber | 156/167 |
| 4,091,140 | 5/1978 | Harmon . | |
| 4,096,289 | 6/1978 | Nischwitz et al. | 427/32 |
| 4,103,062 | 7/1978 | Aberson et al. | 428/283 |
| 4,140,607 | 2/1979 | Kreiseimeier et al. | 204/168 |
| 4,170,304 | 10/1979 | Huke . | |
| 4,178,157 | 12/1979 | van Turnhout et al. | 55/155 |
| 4,185,972 | 1/1980 | Nitta et al. . | |
| 4,196,245 | 4/1980 | Kitson et al. | 428/198 |
| 4,208,366 | 6/1980 | Kinney . | |
| 4,209,563 | 6/1980 | Sisson | 428/288 |
| 4,215,682 | 8/1980 | Kubik et al. | 128/205.29 |
| 4,223,677 | 9/1980 | Anderson | 128/287 |
| 4,273,635 | 6/1981 | Beraud et al. | 204/165 |
| 4,298,440 | 11/1981 | Hood | 204/165 |
| 4,305,797 | 12/1981 | Knoll et al. | 204/180 R |
| 4,307,143 | 12/1981 | Meitner | 252/91 |
| 4,308,223 | 12/1981 | Stern | 264/22 |
| 4,310,478 | 1/1982 | Balslev et al. . | |
| 4,323,374 | 4/1982 | Shinagawa et al. . | |
| 4,324,198 | 4/1982 | Muz | 118/630 |
| 4,340,563 | 7/1982 | Appel et al. | 264/518 |
| 4,342,812 | 8/1982 | Selwood | 428/286 |
| 4,353,799 | 10/1982 | Leonard | 210/321.3 |
| 4,357,234 | 11/1982 | Inculet et al. | 209/127 B |
| 4,363,682 | 12/1982 | Thiebault . | |
| 4,363,723 | 12/1982 | Knoll et al. | 209/128 |
| 4,373,224 | 2/1983 | Bandai et al. . | |
| 4,374,727 | 2/1983 | Takahashi et al. | 209/127 B |
| 4,374,888 | 2/1983 | Bornslaeger | 428/198 |
| 4,375,718 | 3/1983 | Wadsworth et al. | 29/592 |
| 4,392,876 | 7/1983 | Schmidt . | |
| 4,394,235 | 7/1983 | Brandt et al. . | |
| 4,411,795 | 10/1983 | Olson | 210/679 |
| 4,430,277 | 2/1984 | Lin . | |
| 4,443,513 | 4/1984 | Meitner et al. | 422/195 |
| 4,443,515 | 4/1984 | Atlas | 428/224 |
| 4,451,589 | 5/1984 | Morman et al. | 523/124 |
| 4,455,195 | 6/1984 | Kinsley | 162/13 |
| 4,455,237 | 6/1984 | Kinsley | 210/767 |
| 4,456,648 | 6/1984 | Adamse et al. | 428/283 |
| 4,492,633 | 1/1985 | Sandulyak et al. . | |
| 4,507,539 | 3/1985 | Sando et al. | 219/121 PY |
| 4,513,049 | 4/1985 | Yamasaki et al. . | |
| 4,514,289 | 4/1985 | Inculet | 209/127.3 |
| 4,517,143 | 5/1985 | Kisler . | |
| 4,534,918 | 8/1985 | Forrest, Jr. . | |
| 4,547,420 | 10/1985 | Krueger et al. | 428/229 |
| 4,551,378 | 11/1985 | Carey, Jr. | 428/198 |
| 4,554,207 | 11/1985 | Lee | 428/288 |
| 4,555,811 | 12/1985 | Shimalla | 2/51 |
| 4,588,537 | 5/1986 | Klaase et al. | 264/22 |
| 4,592,815 | 6/1986 | Nakao | 204/165 |
| 4,594,626 | 6/1986 | Frangesh . | |
| 4,618,524 | 10/1986 | Groitzsch et al. | 428/198 |
| 4,622,259 | 11/1986 | McAmish et al. | 428/171 |
| 4,623,438 | 11/1986 | Felton et al. | 204/168 |
| 4,626,263 | 12/1986 | Inoue et al. . | |
| 4,652,282 | 3/1987 | Ohmori et al. | 55/155 |
| 4,652,322 | 3/1987 | Lim | 156/181 |
| 4,657,639 | 4/1987 | Mahadevan et al. . | |
| 4,657,804 | 4/1987 | Mays et al. | 428/212 |
| 4,663,220 | 5/1987 | Wisneski | 428/221 |
| 4,670,913 | 6/1987 | Morell et al. | 2/227 |
| 4,671,943 | 6/1987 | Wahlquist . | |
| 4,677,017 | 6/1987 | DeAntonis et al. | 428/214 |
| 4,689,241 | 8/1987 | Richart et al. | 427/28 |
| 4,699,823 | 10/1987 | Kellenberger et al. | 428/219 |
| 4,705,151 | 11/1987 | Eldridge . | |
| 4,707,398 | 11/1987 | Boggs | 428/224 |
| 4,720,415 | 1/1988 | VanderWielen et al. | 428/152 |
| 4,729,371 | 3/1988 | Krueger et al. | 128/206.19 |
| 4,738,772 | 4/1988 | Giesfeldt | 209/2 |
| 4,739,882 | 4/1988 | Parikh et al. . | |
| 4,749,348 | 6/1988 | Klaase et al. | 425/174.8 |
| 4,761,326 | 8/1988 | Barnes et al. | 428/219 |
| 4,789,504 | 12/1988 | Ohmori et al. . | |
| 4,795,668 | 1/1989 | Krueger et al. | 428/174 |
| 4,797,201 | 1/1989 | Kuppers et al. | 209/127.4 |
| 4,797,318 | 1/1989 | Brooker et al. . | |
| 4,818,464 | 4/1989 | Lau | 264/510 |
| 4,826,703 | 5/1989 | Kisler | 427/466 |
| 4,831,664 | 5/1989 | Suda . | |
| 4,847,914 | 7/1989 | Suda . | |
| 4,859,266 | 8/1989 | Akasaki et al. | 156/273.1 |
| 4,863,785 | 9/1989 | Berman et al. | 428/218 |
| 4,863,983 | 9/1989 | Johnson et al. | 524/140 |
| 4,874,399 | 10/1989 | Reed et al. | 55/2 |
| 4,874,659 | 10/1989 | Ando et al. | 428/221 |
| 4,883,052 | 11/1989 | Weiss et al. . | |
| 4,886,527 | 12/1989 | Fottinger et al. | 55/156 |
| 4,894,131 | 1/1990 | Jacobs et al. | 204/165 |
| 4,901,370 | 2/1990 | Suda . | |
| 4,904,174 | 2/1990 | Moosmayer et al. . | |
| 4,917,942 | 4/1990 | Winters | 428/286 |
| 4,920,168 | 4/1990 | Nohr et al. | 524/188 |

| | | | | | | |
|---|---|---|---|---|---|---|
| 4,944,854 | 7/1990 | Felton et al. | 204/168 | 5,238,733 | 8/1993 | Joseph et al. | 428/284 |
| 4,948,515 | 8/1990 | Okumura et al. | 210/748 | 5,244,482 | 9/1993 | Hassenboehler, Jr. | 55/528 |
| 4,948,639 | 8/1990 | Brooker et al. | 428/35.2 | 5,246,637 | 9/1993 | Matsuura et al. . |
| 4,960,820 | 10/1990 | Hwo | 524/528 | 5,247,072 | 9/1993 | Ning et al. | 536/97 |
| 4,965,122 | 10/1990 | Morman | 428/225 | 5,254,297 | 10/1993 | Deeds . |
| 4,983,677 | 1/1991 | Johnson et al. | 525/127 | 5,256,176 | 10/1993 | Matsuura et al. | 55/528 |
| 5,012,094 | 4/1991 | Hamade . | | 5,257,982 | 11/1993 | Cohen et al. | 604/378 |
| 5,021,501 | 6/1991 | Ohmori et al. | 524/544 | 5,264,276 | 11/1993 | McGregor et al. | 428/252 |
| 5,032,419 | 7/1991 | Lamirand et al. | 427/470 | 5,284,703 | 2/1994 | Everhart et al. | 428/283 |
| 5,035,941 | 7/1991 | Blackburn | 428/286 | 5,286,326 | 2/1994 | Greve | 156/272.4 |
| 5,051,159 | 9/1991 | Togashi et al. | 204/165 | 5,294,482 | 3/1994 | Gessner . |
| 5,055,151 | 10/1991 | Duffy . | | 5,306,534 | 4/1994 | Bosses | 428/35.2 |
| 5,057,710 | 10/1991 | Nishiura et al. | 307/400 | 5,308,674 | 5/1994 | Zafiroglu | 428/102 |
| 5,062,158 | 11/1991 | Oka et al. | 2/46 | 5,308,691 | 5/1994 | Lim et al. | 428/286 |
| 5,077,468 | 12/1991 | Hamade . | | 5,336,545 | 8/1994 | Morman | 428/152 |
| 5,090,975 | 2/1992 | Requejo et al. . | | 5,350,620 | 9/1994 | Sundet et al. | 428/172 |
| 5,110,620 | 5/1992 | Tani et al. | 427/40 | 5,389,202 | 2/1995 | Everhart et al. | 162/103 |
| 5,112,048 | 5/1992 | Deeds . | | 5,397,413 | 3/1995 | Trimble et al. | 156/167 |
| 5,112,677 | 5/1992 | Tani et al. . | | 5,401,446 | 3/1995 | Tsai | 264/22 |
| 5,118,942 | 6/1992 | Hamade | 250/324 | 5,407,581 | 4/1995 | Onodera et al. | 210/654 |
| 5,135,724 | 8/1992 | Dinter et al. . | | 5,409,766 | 4/1995 | Yuasa et al. | 428/224 |
| 5,138,971 | 8/1992 | Nakajima et al. . | | 5,411,576 | 5/1995 | Jones et al. | 95/57 |
| 5,143,767 | 9/1992 | Matsuura et al. . | | 5,436,033 | 7/1995 | Mino et al. . |
| 5,149,335 | 9/1992 | Kellenberger et al. | 604/372 | 5,436,066 | 7/1995 | Chen | 428/288 |
| 5,156,902 | 10/1992 | Pieper et al. | 604/370 | 5,441,550 | 8/1995 | Hassenboehler, Jr. | 55/486 |
| 5,165,979 | 11/1992 | Watkins et al. | 428/113 | 5,443,606 | 8/1995 | Hassenboehler, Jr. | 55/486 |
| 5,169,706 | 12/1992 | Collier, IV et al. | 428/152 | 5,455,108 | 10/1995 | Quincy et al. | 428/266 |
| 5,173,356 | 12/1992 | Eaton et al. | 428/219 | 5,456,972 | 10/1995 | Roth et al. | 428/224 |
| 5,178,932 | 1/1993 | Perkins et al. | 428/198 | 5,464,688 | 11/1995 | Timmons et al. . |
| 5,183,701 | 2/1993 | Jacobs et al. | 428/229 | 5,468,428 | 11/1995 | Hanschen et al. . |
| 5,188,885 | 2/1993 | Timmons et al. | 428/198 | 5,472,481 | 12/1995 | Jones et al. | 96/15 |
| 5,204,174 | 4/1993 | Daponte et al. | 428/286 | 5,482,765 | 1/1996 | Bradley et al. . |
| 5,206,061 | 4/1993 | Ando et al. | 428/34.7 | 5,486,411 | 1/1996 | Hassenboehler, Jr. et al. | 428/286 |
| 5,213,881 | 5/1993 | Timmons et al. | 428/224 | 5,491,022 | 2/1996 | Smith | 428/224 |
| 5,213,882 | 5/1993 | Sassa et al. | 428/224 | 5,493,117 | 2/1996 | Tamaki et al. | 264/483 |
| 5,226,992 | 7/1993 | Morman | 156/62.4 | 5,496,507 | 3/1996 | Angadjivand et al. | 264/423 |
| 5,230,727 | 7/1993 | Pound et al. | 55/492 | 5,503,745 | 4/1996 | Ogata et al. | 210/490 |
| 5,232,770 | 8/1993 | Joseph | 428/284 | | | |

NONWOVEN BARRIER AND METHOD OF MAKING THE SAME

This application is a continuation of application Ser. No. 08/266,293 entitled "IMPROVED NONWOVEN BARRIER AND METHOD OF MAKING THE SAME" and filed in the U.S. Patent and Trademark Office on Jun. 27, 1994, now abandoned. The entirety of this Application is hereby incorporated by reference.

FIELD OF THE INVENTION

The present invention is directed to bacterial barrier fabrics. More particularly, the present invention is directed to nonwoven bacterial barrier fabrics for use as, for example, sterilization wrap, surgical draping, surgical gowns, cover garments, such as over-suits, and the like.

BACKGROUND OF THE INVENTION

As is generally known, surgical gowns, surgical drapes, surgical face masks and sterile wrap (hereinafter collectively "surgical articles") have been designed to greatly reduce, if not prevent, the transmission through the surgical article of liquids and/or airborne contaminates. In surgical procedure environments, such liquid sources include the gown wearer's perspiration, patient liquids, such as blood and life support liquids such as plasma and saline. Examples of airborne contaminates include, but are not limited to, biological contaminates, such as bacteria, viruses and fungal spores. Such contaminates may also include particulate material such as, but not limited to, lint, mineral fines, dust, skin squares and respiratory droplets. A measure of a fabrics ability to prevent the passage of such airborne materials is sometimes expressed in terms of "filtration efficiency".

Many of these surgical articles were originally made of cotton or linen and were sterilized prior to their use in the operating room. Such surgical articles fashioned from these materials, however, permitted transmission or "strike-through" of various liquids encountered in surgical procedures. In these instances, a path was established for transmission of biological contaminates, either present in the liquid or subsequently contacting the liquid, through the surgical article. Additionally, in many instances surgical articles fashioned from cotton or linen provide insufficient barrier protection from the transmission therethrough of airborne contaminates. Furthermore, these articles were costly, and, of course, laundering and sterilization procedures were required before reuse.

Disposable surgical articles have largely replaced linen surgical articles. Advances in such disposable surgical articles include the formation of such articles from totally liquid repellent fabrics which prevent strike-through. In this way, biological contaminates carried by liquids are prevented from passing through such fabrics. However, in some instances, surgical articles formed from nonporous films, while being liquid and airborne contaminate impervious, may retain body heat and moisture and thus may become over a period of time, uncomfortable to wear.

In some instances, surgical articles fashioned from liquid repellent fabrics, such as fabrics formed from nonwoven polymers, sufficiently repel liquids and are more breathable and thus more comfortable to the wearer than nonporous materials. However, these improvements in comfort and breathability provided by such nonwoven fabrics have generally occurred at the expense of barrier properties or filtration efficiency.

While the focus thus far has been directed to surgical articles, there are many other garment or over-garment applications, such as personal protective equipment applications, whose designers require both fabric comfort and filtration efficiency. Other personal protective equipment applications include, but are not limited to, laboratory applications, clean room applications, such as semi-conductor manufacture, agriculture applications, mining applications, and environmental applications.

Therefore, there is a need for garment materials and methods for making the same which provide improved breathability and comfort as well as improved filtration efficiency. Such improved materials and methods are provided by the present invention and will become more apparent upon further review of the following specification and claims.

SUMMARY OF THE INVENTION

In response to the above problems encountered by those of skill in the art, the present invention provides an ethylene oxide sterilizable polymer web, such as, for example, a nonwoven fabric. The webs of the present invention are formed by subjecting a portion of the web to charging, and more particularly to electrostatic charging, and then ethylene oxide sterilizing the web. The web may be subjected to charging followed by ethylene oxide sterilization or ethylene oxide sterilization followed by charging. The web may also be treated with an antistatic material before or after subjecting the web to charging.

The above web may further include a second web in a juxtaposed relationship to the first web. The second web may be formed from polymer fibers wherein a portion of these fibers may be subjected to charging. An antistatic treatment may also be present about portions of the second web.

DETAILED DESCRIPTION OF THE INVENTION

Disclosed herein are compositions, and methods of making the same, which improved both the airborne contaminate barrier and filtration efficiency of a web. The web of the present invention may be formed from polymer fibers, films, foams or a combination thereof. The films and foams may be porous or non-porous.

Among the applications for such compositions and methods are included, but not limited to, applications requiring sterilizable, breathable materials having high airborne contaminate barrier properties. Such materials have application in surgical articles, such as gowns, drapes, sterile wrap and face mask, as well as other non-surgical applications such as agriculture, mining, clean room and environmental.

Polymers, and particularly thermoplastic polymers, are well suited for the formation of webs which are useful in the practice of the present invention. Nonwoven webs useful in present invention can be made from a variety of processes including, but not limited to, air laying processes, wet laid processes, hydroentangling processes, spunbonding, meltblowing, staple fiber carding and bonding, and solution spinning.

The materials suitable for forming webs of the present invention include a variety of dielectric materials such as, but not limited to, polyesters, polyolefins, nylon and copolymers, polymer blends and bi-component polymers of these materials. In the case of nonwoven webs formed from fibers, the fibers may be relatively short, staple length fibers, typically less than 3 inches, or longer more continuous fibers such as are produced by a spunbonding process.

It has been found that nonwoven webs formed from polyolefin-based fibers are particularly well-suited for the above applications. Examples of such nonwovens are the polypropylene nonwovens produced by Kimberly-Clark Corporation. And more particularly, a three layered spunbond, meltblown, spunbond material (SMS) produced by Kimberly-Clark Corporation.

This spunbond, meltblown, spunbond material may be made from three separate layers which are laminated to one another. Such a method of making this laminated material is described in commonly assigned U.S. Pat. No. 4,041,203 to Brock et al which is herein incorporated by reference. Alteratively, the spunbond, meltblown, spunbond material may be made by first forming a spunbond, meltblown laminate. The spunbond, meltblown laminate is formed by applying a layer of meltblown on to a layer of spunbond. The second layer of spunbond is then applied to the meltblown side of the previously formed spunbond, meltblown laminate. Generally, the two outer layers provide the nonwoven fabric with strength while the inner layer provides barrier properties.

Suitable webs may be formed from a single layer or multiple layers. In the case of multiple layers, the layers are generally positioned in a juxtaposed or surface-to-surface relationship and all or a portion of the layers may be bound to adjacent layers. In the case of a nonwoven web, the nonwoven web may be formed from a plurality of separate nonwoven webs wherein the separate nonwoven webs may be formed from single or multiple layers. In those instances where the web includes multiple layers, the entire thickness of the web may be subjected to charging or individual layers may be separately subjected to charging and then combined with other layers in a juxtaposed relationship to form the finished web.

There are many well known methods of subjecting a material to charging, and particularly electrostatic charging. These well known methods include, for example, thermal, liquid-contact, electron beam and corona discharge methods. The method used for electrostatically charging the materials discussed in the Examples 1 and 2 (below) is the technique disclosed in U.S. patent application No. 07/958,958 filed Oct. 9, 1992 which is assigned to the University of Tennessee, and is herein incorporated by reference. This technique involves subjecting a material to a pair of electrical fields wherein the electrical fields have opposite polarities.

Sterilization of the web may also be accomplished by ethylene' oxide sterilization. In those instances when it is desired to sterilize surgical instruments by ethylene oxide, the surgical instruments may be wrapped in a nonwoven web. The entire package may then be subjected to an ethylene oxide sterilization cycle. When the ethylene oxide sterilization cycle is completed, the instruments, still wrapped, are then removed from the ethylene oxide sterilizing equipment and are stored in the wrapping material until-needed. When needed, the wrapping web is removed making the instruments available for handling.

The ethylene oxide sterilization cycle may vary dependent upon type of sterilizer and the size/quantity of the items being sterilized. In the Examples described below, ethylene oxide sterilization was accomplished by using either a RSSA Chamber J88-39 or J88-59, made by Vacu Dyne, Ill. Generally, the ethylene oxide sterilization cycle includes a preconditioning phase, a sterilization phase and a de-gassing phase. The process parameters for each of these phases are provided below.

| Process Parameters | Set Point |
| --- | --- |
| A. PRECONDITIONING | |
| Temperature | 115° F. |
| Relative Humidity | 63% |
| Holding time | 18 hours |
| B. STERILIZATION | |
| Chamber Temperature during exposure | 130.0 F. |
| Chamber Temperature at all other times | 130.0 F. |
| Initial Evacuation | 1.2" Absolute |
| Leak Test | 1.2" Absolute |
| Leak Test Dwell | 5 minutes |
| Nitrogen Dilution | 3.2" Absolute |
| Evacuation | 1.2" Absolute |
| Humidity Injection Pressure Increase to | 2.9" Absolute |
| Humidification Dwell Time | 30 minutes |
| ETC Injection Pressure | 15" Absolute |
| Time to inject gas | NA |
| Cycle Exposure | 2 hours |
| Exposure Pressure | 15" Absolute |
| Exposure Temperature | 130.0 F. |
| 1st Re-evacuation | 6.0" Absolute |
| 1st Nitrogen Inbleed | 50.0" Absolute |
| 2nd Re-evacuation | 1.6" Absolute |
| 2nd Nitrogen Inbleed | 50.0" Absolute |
| 3rd Re-evacuation | 1.6" Absolute |
| 3rd Nitrogen Inbleed | 50.0" Absolute |
| 4th Re-evacuation | 1.6" Absolute |
| Air Inbleed | To Atmospheric Pressure |
| C. DEGASSING PARAMETERS | |
| Degassing Time | 24.0 hours |
| Degassing Temperature | 130° F. |

In those instances where the web is used in or around flammable materials or static charge build-up and/or discharge is a concern, the web may be treated with any number of antistatic materials. In these instances, the antistatic material may be applied to the web by any number of well known techniques including, but not limited to dipping the web into a solution containing the antistatic material or by spraying the web with a solution containing the antistatic material. In some instances the antistatic material may be applied to both the external surfaces of the web and the bulk of the web. In other instances, the antistatic material may be applied to portions of the web, such as a selected surface or surfaces thereof.

Of particular usefulness as an antistatic material is an alcohol phosphate salt product known as ZELEC® and available from the Du Pont Corporation. The web may be treated with the antistatic material either before or after subjecting the web to charging. Furthermore, some or all of the material layers may be treated with the antistatic material. In those instances where only some of the material layers are treated with antistatic material, the non-treated layer or layers may be subjected to charging prior to or after combining with the antistatic treated layer or layers.

To demonstrate the attributes of the present invention, the following Examples are provided.

EXAMPLE 1

Kimberly-Clark manufactures a series of single sheet laminate nonwoven web materials made from three layers of fibrous material, i.e., spunbond-meltblown-spunbond (SMS) layers. These materials are available in a variety of basis weights. The two nonwoven webs used in these Examples were such single sheet laminate materials sold by Kimberly-Clark. Each of the nonwoven webs had a basis weight of 2.2 osy (ounces per square yard). Both spunbond layers had a basis weight of 0.85 osy and the meltblown layer had a basis weight of 0.50 osy. One of the nonwoven webs was a ZELEC® treated laminate and is sold by Kimberly-Clark under the mark KIMGUARD™ Heavy Duty Sterile Wrap and is designated in Table I as "KIMGUARD™".

The other nonwoven web, designated in Table I as "RSR" also had a basis weight of 2.2 osy but was not treated with an antistatic material. Both spunbond layers had a basis weight of 0.85 osy and the meltblown layer had a basis weight of 0.50 osy.

The method used to subject these webs to electrostatic charging (electret treating) is described in the above referenced U.S. patent application No. 07/958,958.

The surface charge for both KIMGUARD™ and RSR fabrics were analyzed and the data reported in Table I. The charge data for each side of these fabrics was recorded for both before ("AS RECEIVED") and after charging ("ELECTRETED"). Charge data were also recorded for ethylene oxide sterilized fabric samples which were first charged and then ethylene oxide sterilized ("AFTER EO TREATMENT"). As noted in Example 1, the KIMGUARD™ samples were treated with ZELEC™ and the RSR samples were not. Charge measurements were taken at 36 separate surface locations on each sample. For the categories, i.e., "AS RECEIVED" and "ELECTRETED", the KIMGUARD™ and RSR samples were each single large sheets of material. Each such sheets were then portioned into several smaller samples. Sterilization and filtration data reported in Example 2 were derived from these smaller samples.

Charge measurements reported are averaged values of positive (+) or negative (−) volts per cm$^2$. The equipment used to measure charge was an Electrostatic Voltmeter (Trek Model 344, Trek, Inc, Median, N.Y.).

TABLE I

| Material | Side | As Received | Electreted | After EO Treatment Sample 1 | Sample 2 | Sample 3 |
|---|---|---|---|---|---|---|
| KIMGUARD® | A | −2.8 | −125 | −4.2 | 27.2 | — |
| (ZELEC®) | B | +1.6 | −15 | 24.1 | −5.4 | — |
| RSR | A | −61 | +272 | −89 | −130 | −138 |
| (Non-ZELEC®) | B | −87 | −432 | −90 | −46 | +54 |

As illustrated by the above data, the ethylene oxide sterilization process generally diminished the overall surface charge for both the electret treated KIMGUARD™ and the RSR material.

EXAMPLE 2

A summary of the average bacterial filtration efficiency (BFE) test results and standard deviation (SD) are reported for the two categories investigated for KIMGUARD™ in Table II. The first category, reported in Table II is the "Nelson BFE". "Nelson BFE" stands for Nelson Laboratory's (Salt Lake City, Utah) bacterial filtration efficiency test. The procedure used to determine these BFEs is described in Nelson Laboratories' Protocol No. ARO/007B in accordance with MIL Spec 36954C, 4.4.1.1.1 and 4.4.1.2. This category includes the average BFE for 11 KIMGUARD™ fabric samples which were electret-treated then ethylene oxide-sterilized ("KIMGUARD™/Electret/EO") and 11 non-electret-treated KIMGUARD™ fabric samples which were ethylene oxide-sterilized ("KIMGUARD™/EO").

The second category reported in Table II is "Microbial Challenge BFE". This category includes the average BFEs for the KIMGUARD™ samples.

The Microbial Challenge BFE procedure utilized a six port exposure chamber. Five of the ports accommodated five separate samples. The challenge control filter material was positioned in the sixth port. Three conditions were maintained in the microbial challenge test. These were: first, a 2.8 LPM (Liters Per Minute) flow rate through each of the ports; second, an exposure time of fifteen minutes followed by a chamber exhaust of fifteen minutes, and; third, a microbial challenge that results in 1×10$^6$ CFU's (Colony Forming Units) per port. Bacillus subtilis ss globigii spores, purchased from Amsco (Part No. NA-026, P-764271-022) were used to make the working spore suspension of 1×10$^6$ CFUs per port recovery.

The value reported is an expression of the reduction of number of colony forming units (CFUs) or bacteria passing through a sample compared to the number CFUs passing through the challenge control filter material. This value was derived by subtracting the number of CFUs passing through a sample from the number of CFUs passing through the challenge control filter material. The difference in the number of CFUs passing through these materials is then divided by the number of CFUs passing through the challenge filter material and then multiplied by 100 to convert to percent.

TABLE II

| Sample | Nelson BFE | Microbial Challenge BFE |
|---|---|---|
| KIMGUARD ®/Electret/EO | 97.51 +/− 0.39 | 96.44 +/− 4.51 |
| KIMGUARD ®/EO | 89.96 +/− 1.04 | 79.04 +/− 6.50 |

Table III summarizes the average Nelson BFE and the Microbial Challenge BFE categories for the RSR nonwoven materials. The procedures for both the Nelson BFE and identical to the Nelson BFE and Microbial Challenge BFE procedures describe above. "RSR/Electret/EO" stands for RSR electret-treated then ethylene oxide-treated samples. "RSR/Electret" stands for RSR electret-treated samples. "RSR/EO" stands for RSR ethylene oxide-sterilized samples. 15 samples of each class of RSR material described above were analyzed and the results averaged.

TABLE III

| Sample | Nelson BFE | Microbial Challenge BFE |
|---|---|---|
| RSR/Electret/EO | 96.92 +/− 0.91 | 97.56 +/− 0.83 |
| RSR/Electret | 95.75 +/− 0.60 | 98.91 +/− 0.64 |
| RSR/EO | 79.73 +/− 3.20 | 79.82 +/− 5.96 |

Example 2 demonstrates that barrier properties of an ethylene oxide sterilizable material are improved when such material is first subjected to charging, and particularly electrostatic charging, and then ethylene oxide sterilized as compared to the same material which is not subjected to charging prior to ethylene oxide sterilization. It will be further observed that the decrease in the surface charge which occurred after ethylene oxide sterilization (Table I) did not significantly affect the barrier properties of these materials.

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

What is claimed is:

1. An ethylene oxide sterilized web wherein at least one portion of the web has been subjected to electrostatic charging.

2. The web of claim 1 wherein the web is formed from a nonwoven material which comprises first and second nonwoven webs joined together in juxtaposed relationship.

3. The web of claim 1 having a surface and wherein such surface has a negative charge and wherein the average negative surface charge on the surface is less than 100 volts/cm$^2$.

4. The web of claim 1 having a first and a second surface and wherein these surfaces have a negative charge and wherein the average negative surface charge on the first surface is less than 100 volts/cm$^2$ and wherein the average negative surface charge on the second surface is less than 100 volts/cm$^2$.

5. The web of claim 1 having a surface and wherein such surface has a positive charge and wherein the average positive surface charge on the surface is less than 60 volts/cm$^2$.

6. The web of claim 1 containing an antistatic material.

7. An ethylene oxide sterilized nonwoven web laminate comprising:

two outer layers separated by an intermediate layer, wherein the two outer layers are spunbond nonwoven layers and the intermediate layer is a meltblown layer; and at least one of the layers is subjected to electrostatic charging.

8. The nonwoven web of claim 7 wherein all three layers are subjected to electrostatic charging.

9. The nonwoven web of claim 8 wherein at least one of the layers is treated with an antistatic material.

10. A charged web having a Nelson bacterial filtration efficiency of at least 96%.

11. The charged web of claim 10 wherein the web is an electrostatically charged web.

12. The charged web of claim 10 wherein the web is a nonwoven web.

13. The charged web of claim 12 wherein the nonwoven web comprises two outer layers separated by an intermediate layer wherein the two outer layers are spunbond nonwoven layers and the intermediate layer is a meltblown layer.

14. The charged web of claim 10 containing antistatic material.

15. A web prepared by a process comprising sterilizing a charged web by ethylene oxide sterilization.

16. The web of claim 15 wherein the charged web is an electrostatically charged web.

17. The web of claim 15 wherein the charged web is a nonwoven web.

18. The web of claim 17 wherein the nonwoven web comprises two outer layers separated by an intermediate layer wherein the two outer layers are spunbond nonwoven layers and the intermediate layer is a meltblown layer.

19. The web of claim 15 wherein the process further comprises treatment with an antistatic material.

* * * * *

UNITED STATES PATENT AND TRADEMARK OFFICE
CERTIFICATION OF CORRECTION

PATENT NO. : 5,814,570

DATED : September 29, 1998

INVENTOR(S): Bernard Cohen

It is certified that error appears in the above-identified patent and that said Letters Patent is hereby corrected as shown below:

Column 1, line 30, "squares" should read --squames--;
Column 3, line 48, "ethylene'" should read --ethylene--;
Column 5, line 7, "KIMGUARD™" should read --KIMGUARD®--;
Column 5, line 8, "KIMGUARD™" should read --KIMGUARD®--;
Column 5, line 17, "KIMGUARD™" should read --KIMGUARD®--;
Column 5, lines 24-25, "KIMGUARD™" should read --KIMGUARD®--;
Column 5, line 25, "ZELEC™" should read --ZELEC®--;
Column 5, line 29, "KIMGUARD™" should read --KIMGUARD®--;
Column 5, line 52, "KIMGUARD™" should read --KIMGUARD®--;
Column 5, line 58, "KIMGUARD™" should read --KIMGUARD®--;
Column 5, line 65, "KIMGUARD™" should read --KIMGUARD®--;
Column 5, line 67, "KIMGUARD™" should read --KIMGUARD®--;
Column 6, line 2, "KIMGUARD™" should read --KIMGUARD®--;
Column 6, line 5, "KIMGUARD™" should read --KIMGUARD®--.

Signed and Sealed this

Twentieth Day of April, 1999

Attest:

Q. TODD DICKINSON

*Attesting Officer*   *Acting Commissioner of Patents and Trademarks*